United States Patent
Guryev et al.

(10) Patent No.: US 10,736,847 B2
(45) Date of Patent: Aug. 11, 2020

(54) INVERTING DEVICE FOR LIPOSOME PREPARATION BY CENTRIFUGATION

(71) Applicant: Becton, Dickinson and Company, Franklin Lakes, NJ (US)

(72) Inventors: Oleg Guryev, San Jose, CA (US); Aaron J. Middlebrook, San Jose, CA (US); Marybeth Sharkey, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 132 days.

(21) Appl. No.: 16/026,999

(22) Filed: Jul. 3, 2018

(65) Prior Publication Data
US 2020/0009052 A1    Jan. 9, 2020

(51) Int. Cl.
*A61K 41/00* (2020.01)
*A61K 9/127* (2006.01)
*B01D 61/14* (2006.01)
*B01L 3/00* (2006.01)
*A61K 49/22* (2006.01)

(52) U.S. Cl.
CPC ........ *A61K 9/1277* (2013.01); *A61K 41/0028* (2013.01); *B01D 61/142* (2013.01); *A61K 49/227* (2013.01); *B01L 3/502753* (2013.01); *G01N 2333/00* (2013.01)

(58) Field of Classification Search
None
See application file for complete search history.

(56) References Cited

U.S. PATENT DOCUMENTS

| | | | |
|---|---|---|---|
| 4,737,323 A | | 4/1988 | Martin et al. |
| 5,833,860 A | * | 11/1998 | Kopaciewicz ......... B01D 61/00 |
| | | | 210/650 |
| 6,020,150 A | * | 2/2000 | Contant-Pussard ...... C12Q 1/04 |
| | | | 435/261 |
| 6,544,417 B1 | | 4/2003 | Tortorella |
| 6,623,671 B2 | * | 9/2003 | Coe ...................... A61K 9/1277 |
| | | | 264/4.3 |

FOREIGN PATENT DOCUMENTS

EP    0460720 B1    8/1996

OTHER PUBLICATIONS

Akbarzadeh et al. "Liposome: classification, preparation, and applications," Nanoscale Research Letters, vol. 8, 2013, 102 (9 pages).
Fujii et al. "Liposome display for in vitro selection and evolution of membrane proteins," Nature Protocols, vol. 9, No. 7, 2014, pp. 1578-1591.

(Continued)

*Primary Examiner* — Chester T Barry
(74) *Attorney, Agent, or Firm* — Kathleen Y. Rao; Bret E. Field; Bozicevic, Field & Francis LLP

(57) ABSTRACT

Methods and devices for producing a population of liposomes are provided. Aspects of the methods include applying a centrifugal force to a suspension of liposomes in a manner sufficient to pass the liposomes through a porous membrane to produce a population of liposomes. Aspects of the invention further include devices, systems and kits useful for performing the methods.

13 Claims, 2 Drawing Sheets

(56) References Cited

OTHER PUBLICATIONS

Guven et al. "Rapid and efficient method for the size separation of homogeneous fluorescein-encapsulating liposomes," Journal of Liposome Research, vol. 19, No. 2, 2009, pp. 148-154.

Hope et al. "Production of large unilamellar vesicles by a rapid extrusion procedure. Characterization of size distribution, trapped volume and ability to maintain a membrane potential," Biochimica et Biophysica Acta, vol. 812, 1985, pp. 55-65.

Hope et al. "Chapter 8: Reduction of liposome size and preparation of unilamellar vesicles by extrusion techniques," *Liposome Technology*, $2^{nd}$ Edition. G. Gregoriadis, Ed., CRI Press, Boca Raton, FL, vol. 1, 1993, pp. 124-139.

Macdonald et al. "Small-volume extrusion apparatus for preparation of large, unilamellar vesicles," Biochimica et Biophysica Acta, vol. 1061, 1991, pp. 297-303.

Mayer et al. "Vesicles of variable sizes produced by a rapid extrusion procedure," Biochimica et Biophysica Acta, vol. 858, 1986, pp. 161-168.

Olson et al. "Preparation of liposomes of defined size distribution by extrusion through polycarbonate membranes," Biochimica et Biophysica Acta, vol. 557, 1979, pp. 9-23.

* cited by examiner

INVERTING DEVICE FOR LIPOSOME PREPARATION BY CENTRIFUGATION

Liposomes are spherical vesicles that have one or multiple lipid bilayers. Liposomes that include a single lipid bilayer may be referred to as unilamellar liposomes, whereas liposomes that include multiple lipid bilayers may be referred to as multilamellar vesicles. Liposomes can be prepared using different methods, which may depend on factors, such as the lipid composition of the lipid bilayer of the liposomes, the type of medium in which the lipid vesicles are dispersed, the desired size of the liposomes, the desired polydispersity of the liposomes, the robustness and batch-to-batch reproducibility of the production method, and other factors, such as the intended use of the resulting liposomes. For example, liposomes may contain a substance, such as a drug, and be used to deliver the substance to a target area in a patient. Thus, the method used to produce such liposomes may also depend on the physicochemical characteristics of the substance to be entrapped in the liposomes, the concentration of the entrapped substance, or additional processes involved during application/delivery of the liposomes to the patient.

After a suspension of liposomes has been produced, such as a suspension of large, multilamellar vesicles, it may be desirable to produce liposomes having sizes within a certain size range. One common technique for sizing liposomes is extrusion, a process by which large, multilamellar vesicles can be disrupted and downsized by extrusion through a polycarbonate membrane with defined pore size.

SUMMARY

In this invention we describe an inverting device designed for the preparation of liposomes by centrifugation. Aspects of this method include applying a centrifugal force to a suspension of liposomes in a manner sufficient to pass the liposomes through a porous membrane to produce a population of liposomes of a known and restricted size. In order to facilitate repeated reciprocal processing the device is symmetrical: two identical collection tubes are connected through porous polycarbonate membrane holding unit. Aspects of the invention further include devices, systems and kits useful for performing the methods.

DETAILED DESCRIPTION

Figure 1:
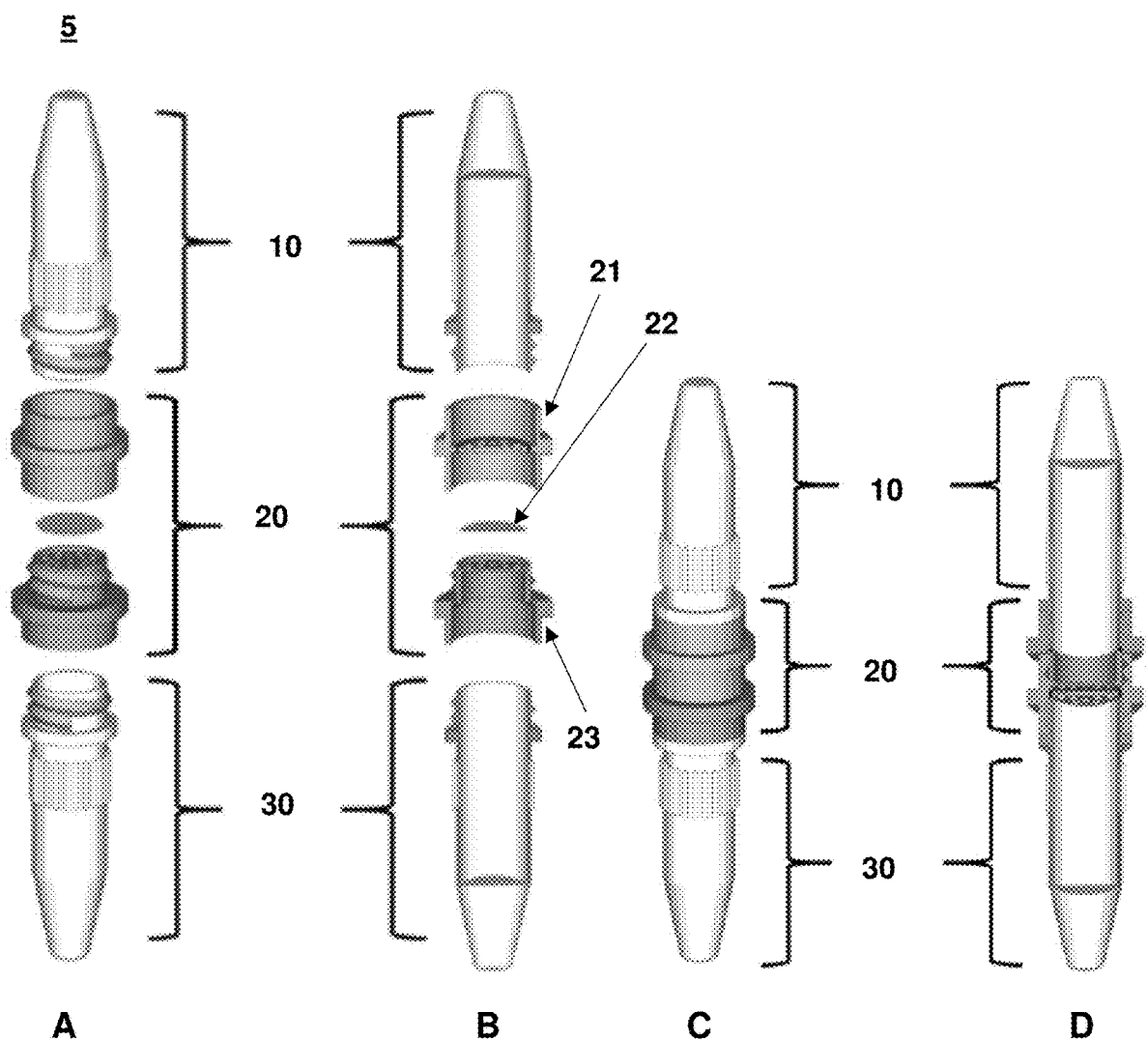
FIG. 1 is an illustration of an inverting liposome extrusion device according to embodiments of the present disclosure.

Methods and devices for producing a population of liposomes are provided. Aspects of the methods include applying a centrifugal force to a suspension of liposomes in a manner sufficient to pass the liposomes through a porous membrane to produce a population of liposomes. Aspects of the invention further include devices, systems and kits useful for performing the methods.

Before embodiments of the present disclosure are described in greater detail, it is to be understood that these embodiments are not limited to the particular embodiments described, as such may vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the embodiments of the present disclosure. The upper and lower limits of these smaller ranges may independently be included in the smaller ranges and are also encompassed within the embodiments of the present disclosure, subject to any specifically excluded limit in the stated range. Where the stated range includes one or both of the limits, ranges excluding either or both of those included limits are also included in the embodiments of the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the embodiments of the present disclosure. Any recited method can be carried out in the order of events recited or in any other order which is logically possible.

As summarized above, the present disclosure provides methods for producing a population of liposomes. In further describing embodiments of the disclosure, the subject methods are first described in greater detail. Next, devices useful for performing the methods are described. In addition, systems, as well as kits that include the subject devices, are also provided.

Methods for Producing Liposomes

Aspects of the present disclosure include methods for producing a population of liposomes. In some instances, the population of liposomes produced by the methods is a population of liposomes of defined size. By "defined size" is meant that, because of the manner in which the liposomes are made, the sizes of the various liposomes in the population are known, and specifically the range of liposome sizes in the population is known. In some cases, the liposomes have an average size that is substantially the same. For example, in the case of spherical liposomes, a population of liposomes may have an average diameter that is substantially the same. By "average" is meant the arithmetic mean. Values that are substantially the same include values that vary from each other by 50% or less, such as 45% or less, or 40% or less, or 35% or less, or 30% or less, or 25% or less, or 20% or less, or 15% or less, or 10% or less, or 5% or less, or 3% or less, or 1% or less, or 0.5% or less. In some cases, values that are substantially the same include values that vary from each other by 10% or less. In some cases, values that are substantially the same include values that vary from each other by 5% or less. In some cases, values that are substantially the same include values that vary from each other by 3% or less. In some cases, values that are substantially the same include values that vary from each other by 1% or less. In some cases, values that are substantially the same include values that vary from each other by 0.5% or less. The average size of the liposomes may, in some instances, vary by 50% or less, such as 45% or less, or 40% or less, or 35% or less, or 30% or less, or 25% or less, or 20% or less, or 15% or less, or 10% or less, or 5% or less, or 3% or less, or 1% or less, or 0.5% or less. In some cases, the average size of the liposomes varies by 10% or less. In some cases, the average size of the liposomes varies by 5% or less. In some cases, the average size of the liposomes varies by 3% or less. In some cases, the average size of the liposomes varies by 1% or less. In some cases, the average size of the liposomes varies by 0.5% or less.

In certain embodiments, a population of liposomes may be described by the polydispersity of the liposomes. "Dispersity" or "polydispersity" is a measure of the heterogeneity of sizes of particles in a mixture. In the context of liposomes, polydispersity can range from 0 to 1, where a polydispersity of 0 indicates a monodisperse population of liposomes (e.g., liposomes that have the same average size), and where a polydispersity of 1 indicates a heterogeneous mixture of liposomes. In some cases, the size of liposomes (and thus the polydispersity) can be determined by dynamic light scattering (DLS).

In certain embodiments, methods of the present disclosure are sufficient for producing a population of liposomes from a suspension of liposomes (e.g., an aqueous suspension of liposomes). In some cases, the starting suspension of liposomes includes a population of liposomes having heterogeneous sizes. As such, methods of the present disclosure include starting with a suspension of liposomes (e.g., a population of liposomes having heterogeneous sizes) and producing a population of liposomes from the starting suspension of liposomes.

In some embodiments, the method includes producing a population of liposomes from a suspension of heterogeneous liposomes, where the average size of the resulting population of liposomes varies by 50% or less, such as 45% or less, or 40% or less, or 35% or less, or 30% or less, or 25% or less, or 20% or less, or 15% or less, or 10% or less, or 5% or less, or 3% or less, or 1% or less, or 0.5% or less. In some cases, the method includes producing a population of liposomes from a suspension of heterogeneous liposomes, where the average size of the resulting population of liposomes varies by 10% or less. In some cases, the method includes producing a population of liposomes from a suspension of heterogeneous liposomes, where the average size of the resulting population of liposomes varies by 5% or less. In some cases, the method includes producing a population of liposomes from a suspension of heterogeneous liposomes, where the average size of the resulting population of liposomes varies by 3% or less. In some cases, the method includes producing a population of liposomes from a suspension of heterogeneous liposomes, where the average size of the resulting population of liposomes varies by 1% or less. In some cases, the method includes producing a population of liposomes from a suspension of heterogeneous liposomes, where the average size of the resulting population of liposomes varies by 0.5% or less. In yet other instances, the average size of the disparate liposome members of the population may vary by 50% or more, such as 75% or more, including 100% or more. For instance, the average size of the disparate liposome members in the starting suspension of liposomes may vary by 50% or more, such as 75% or more, including 100% or more.

In some instances, the starting suspension of liposomes has a higher polydispersity as compared to the produced population of liposomes. Thus, methods of the present disclosure are useful for producing a population of liposomes having a polydispersity less than the polydispersity of the starting suspension of liposomes.

In some cases, the polydispersity of the produced population of liposomes is 0.9 or less, such as 0.8 or less, or 0.7 or less, or 0.5 or less, or 0.4 or less, or 0.3 or less, or 0.2 or less, or 0.1 or less, or 0.05 or less, or 0.01 or less. For example, the polydispersity of the produced population of liposomes may be 0.5 or less. In some cases, the polydispersity of the produced population of liposomes may be 0.4 or less. In some cases, the polydispersity of the produced population of liposomes may be 0.3 or less. In some cases, the polydispersity of the produced population of liposomes may be 0.2 or less. In some cases, the polydispersity of the produced population of liposomes may be 0.1 or less. In some cases, the polydispersity of the produced population of liposomes may be 0.05 or less. In some cases, the polydispersity of the produced population of liposomes may be 0.01 or less. In certain instances, the polydispersity of the produced population of liposomes ranges from 0.01 to 0.5, such as 0.01 to 0.4, or 0.01 to 0.3, or 0.01 to 0.2, or 0.01 to 0.1. In other embodiments, the polydispersity of the produced population of liposomes ranges from 0.01 to 0.5, such as 0.05 to 0.5, or 0.1 to 0.5, or 0.1 to 0.4, or 0.1 to 0.3. In other embodiments, the polydispersity of the produced population of liposomes ranges from 0.01 to 0.5, such as 0.05 to 0.5, or 0.1 to 0.5, or 0.2 to 0.5, or 0.2 to 0.4.

In some cases, the polydispersity of the starting suspension of liposomes is 0.5 or more, such as 0.6 or more, or 0.7 or more, or 0.8 or more, or 0.9 or more. In some cases, the polydispersity of the starting suspension of liposomes is 1. For example, the polydispersity of the starting suspension of liposomes may range from 0.5 to 1, such as 0.6 to 1, or 0.7 to 1, or 0.8 to 1, or 0.9 to 1.

In some instances, the starting suspension of liposomes includes liposomes having sizes larger than the produced population of liposomes. In some instances, the starting suspension of liposomes includes liposomes having an average size (e.g., an average diameter) of 500 nm or more, such as 600 nm or more, or 700 nm or more, or 800 nm or more, or 900 nm or more, or 1000 nm or more, or 1250 nm or more, or 1500 nm or more, or 1750 nm or more, or 2000 nm or more, or 2250 nm or more, or 2500 nm or more, or 2750 nm or more, or 3000 nm or more, where in some instances the size is 5000 nm or less, such as 4000 nm or less, including 3000 nm or less. For example, the starting suspension of liposomes may include large multilamellar vesicles (LMVs), e.g., multilamellar vesicles having an average size of 200 nm or more, such as ranging from 200 nm to 3,000 nm. In some instances, the starting suspension of liposomes may include large unilamellar vesicles (LUVs), e.g., unilamellar vesicles having an average size of 100 nm or more, such as ranging from 100 nm to 1000 nm.

In some cases, embodiments of the methods may include a step of producing the starting suspension of liposomes. As described above, the suspension of liposomes may be heterogeneous with respect to the sizes of the liposomes in the suspension of liposomes. The suspension of heterogeneous liposomes may be produced using any convenient method for producing liposomes, such as, but not limited to, a solvent dispersion process (e.g., Bangham method, which includes the dissolution of lipids in an organic solvent and then removal of the organic solvent, such as by evaporation of the organic solvent), a detergent removal process (e.g., where detergent-lipid micelles are formed, followed by removal of the detergent to form the liposomes), an injection process (e.g., where lipids are dissolved in an organic solvent and the resulting lipid solution is injected into an aqueous media), a microfluidic process (e.g., where a stream of lipids dissolved in an organic solvent is passed between two aqueous streams in a microfluidic channel), a mechanical dispersion process, a sonication process, combinations thereof, and the like.

Liposomes useful in embodiments of the present disclosure are composed of lipids. In certain embodiments, the lipids are amphiphilic. Amphiphilic lipids may include a hydrophilic group and one or more lipophilic groups covalently bonded to the hydrophilic group. In some cases, the hydrophilic group is a charged group, such as an anionic group or a cationic group. In some instances, the hydrophilic group is an uncharged, polar group. In some embodiments, the hydrophilic group includes a charged group and a polar group. Examples of hydrophilic groups include, but are not limited to, phosphate, phosphocholine, phosphoglycerol, phosphoethanolamine, phosphoserine, phosphoinositol, ethylphosphorylcholine, polyethyleneglycol, polyglycerol, sphingosine, phosphoshingosine, tri-nitrilotriacetic acid, melamine, glucosamine, trimethylamine, spermine, spermidine, and conjugated carboxylates, sulfates, boric acid, sulfonates, sulfates, carbohydrates, amino acids, and the like. In some cases, the hydrophilic group includes phosphocholine.

In certain embodiments, the lipophilic group includes an aliphatic chain, such as a saturated or unsaturated, linear or branched, substituted or unsubstituted aliphatic chain. For example, the lipophilic group may include an aliphatic chain of 2 to 40 carbon atoms in length, and may be saturated or unsaturated, linear or branched, substituted or unsubstituted. For instance, the lipophilic group may include a saturated or unsaturated, linear or branched, substituted or unsubstituted hydrocarbon chain having from 2 to 40 carbon atoms, such as from 4 to 30 carbon atoms, or from 4 to 25 carbon atoms, or from 6 to 24 carbon atoms, or from 10 to 20 carbon atoms. In certain cases, the lipophilic group includes a saturated or unsaturated, linear or branched hydrocarbon chain having 18 carbon atoms. In certain cases, the lipophilic group includes a saturated or unsaturated, linear or branched hydrocarbon chain having 16 carbon atoms. In embodiments where the lipid includes more than one lipophilic group, the lipophilic groups may be the same, or in other cases may be different. Liposomes may be composed of the same type of lipid or combinations of two or more different types of lipids.

Embodiments of the liposomes may include liposomes having a detectable label. In some cases, the detectable label is stably associated with a support. By "stably associated" is meant that a moiety is bound to or otherwise associated with another moiety or structure under standard conditions. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. In certain embodiments, the detectable label is covalently bound to the liposome. For instance, as described above, lipids that comprise the liposome may include a hydrophilic group, which, in some cases may include an activated functional group that provides for a covalent attachment to the detectable label. Any convenient activated functional group useful in chemical synthesis may be used to covalently bond the detectable label to the hydrophilic group of a lipid, such as, but not limited to, amine, carboxyl, amide, hydroxy, azide, maleimide, bromoacetyl, 2-pyridyldithiol, haloalkyl, alkene, or propargyl, or the like.

Liposomes according to embodiments of the present disclosure can include a payload associated with the liposome. As used herein, "payload" refers to a component that is contained within the structure of a liposome, present in a bilayer of lipid particles, or attached to a surface of a liposome (e.g., by a covalent bond or non-covalent interaction). Thus, a payload can include components that are encapsulated by the liposome (e.g., pharmaceutically active agents, nutriceutical agents, cosmeceutical agents, imaging agents, radiopharmaceutical agents, nuclear magnetic resonance contrast agents, and the like). In certain embodiments, the encapsulated payload is in solution, or may be present as a crystal, as a powder, or a combination thereof. For example, in embodiments where it is desired to provide liposomes with an encapsulated payload (e.g., an encapsulated agent, a therapeutic agent, imaging agent, or the like), such agents may be included in an aqueous phase inside the liposome. Alternatively, in embodiments where the agent is hydrophobic and thus less soluble in water, the hydrophobic agent can be included within a portion of the lipid bilayer.

Embodiments of the methods may also include preparing a liposome extrusion device for use in the method of producing a population of liposomes. Generally, a liposome extrusion device according to embodiments of the present disclosure includes a first liquid container, a second liquid container in fluid communication with the first liquid container, a porous membrane, and a component configured to position the membrane between the first liquid container and the second liquid container. More detailed aspects of the liposome extrusion device are described in the Devices section below. The component configured to position the membrane between the first liquid container and the second liquid container may also be referred to herein as a membrane component or a membrane support. In some instances, the membrane component supports the membrane in a position between the first liquid container and the second liquid container. In some cases, the membrane component is removable from the first liquid container. In some cases, the membrane component is removable from the second liquid container. In some cases, the membrane component is removable from both the first liquid container and the second liquid container. As such, embodiments of the method may include positioning the membrane component between the first liquid container and the second liquid container, and thus positioning the membrane between the first liquid container and the second liquid container. For example, the membrane component may be positioned on an open end of the first liquid container and/or on an open end of the second liquid container. Prior to positioning the membrane component on an open end of the first liquid container and/or on an open end of the second liquid container, a suspension of liposomes may be introduced into the liposome extrusion device from which the population of liposomes is produced.

Embodiments of the method for producing a population of liposomes include introducing a suspension of liposomes into the liposome extrusion device. The suspension of liposomes may be introduced into the liposome extrusion device by introducing the suspension of liposomes into either the first liquid container or the second liquid container. For example, in some instances, the suspension of liposomes is introduced into the liposome extrusion device by introducing the suspension of liposomes into the first liquid container. In other instances, the suspension of liposomes is introduced into the liposome extrusion device by introducing the suspension of liposomes into the second liquid container.

In certain embodiments, the method also includes positioning the membrane between the first liquid container and the second liquid container. For instance, since the membrane is supported and contained within the membrane component as described above, the method may include positioning the membrane component between the first liquid container and the second liquid container, which in turn results in positioning the membrane itself between the first liquid container and the second liquid container. In some cases, positioning the membrane includes connecting the membrane component to the first liquid container and/or the second liquid container. For example, the membrane component may be connected to the liquid container containing the suspension of liposomes. In some instances, positioning the membrane includes connecting the membrane component to the first liquid container (e.g., where the first liquid container contains the suspension of liposomes). In some instances, positioning the membrane includes connecting the membrane component to the second liquid container (e.g., where the second liquid container contains the suspension of liposomes). For example, the membrane component may be connected to an open end of the first liquid container and/or the second liquid container. In some cases, the membrane component is connected to an open end of the liquid container containing the suspension of liposomes. For instance, the membrane component may be connected to an open end of the first liquid container. In some instances, the membrane component may be connected to an open end of the second liquid container. Positioning the membrane may further include connecting the other liquid container to the membrane component. For example, positioning the membrane may include connecting the liquid container that is not already connected to the membrane component. The other liquid container may be empty, or in other cases may contain a suspension of liposomes. The membrane component may be connected to an open end of the other liquid container. In some instances, the other liquid container is connected to an end of the membrane component opposing the end where the first liquid container is connected. As such, an assembled liposome extrusion device includes a first liquid container connected to one end of the membrane component and a second liquid container connected to a second opposing end of the membrane component. Either one, or both, the first liquid container or the second liquid container may contain the suspension of liposomes.

In certain embodiments, the first liquid container is in fluid communication with the second liquid container. In some cases, the first liquid container is in fluid communication with the membrane component and the second liquid container. In some cases, the second liquid container is in fluid communication with the membrane component and the first liquid container. In some cases, the first liquid container, the membrane component, and the second liquid container are in fluid communication with each other. By fluid communication is meant that a fluid (e.g., a gas or a liquid, including a suspension of liposomes) is able to flow from one area to another area. For example, in a liposome extrusion device disclosed herein, a fluid may flow from the first liquid container to the second liquid container. Since the membrane is positioned between the first liquid container and the second liquid container, fluid communication between the first liquid container and the second liquid container allows the fluid (e.g., suspension of liposomes) to flow through the membrane as the fluid flows from the first liquid container to the second liquid container or from the second liquid container to the first liquid container.

In certain embodiments, the suspension of liposomes may be introduced into the liposome extrusion device such that the suspension of liposomes is positioned on one side of the membrane. For example, the suspension of liposomes may be contained in the first liquid container, which is positioned on one side of the membrane. During production of the population of liposomes, the suspension of liposomes may traverse from one side of the membrane, through the porous membrane, and to the other side of the membrane. For instance, the suspension of liposomes may be contained initially in the first liquid container on a first side of the membrane and then, during production of the population of liposomes, may traverse the porous membrane to be contained in the second liquid container on the other side of the membrane. In some cases, the suspension of liposomes may be contained initially in the second liquid container on a second side of the membrane and then, during production of the population of liposomes, may traverse the porous membrane to be contained in the first liquid container on the first side of the membrane. In other cases, the suspension of liposomes may be contained initially in both the first liquid container and the second liquid container and then, during production of the population of liposomes, may traverse the porous membrane from either the first liquid container to the second liquid container, or vice versa.

In certain aspects, the suspension of liposomes is introduced into the liposome extrusion device using any convenient liquid handling technique. For example, a volume of the suspension of liposomes may be added to the liposome extrusion device using any convenient liquid handling apparatus, such as, but not limited to, a syringe, a needle, a pipette, an aspirator, among other liquid handling devices.

Methods of the present disclosure are useful for producing a population of liposomes as described above, e.g., a population of liposomes of defined size. In some embodiments, the population of liposomes has an average size less than the average size of the starting suspension of liposomes. In some cases, the produced population of liposomes has an average size (e.g., an average diameter) of 1000 nm or less, such as 900 nm or less, or 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 20 nm or less, or 15 nm or less, or 10 nm or less, or 5 nm or less, or 1 nm or less, where in some instances the size average size is 1 nm or more, such as 5 nm or more. In certain instances, the produced population of liposomes has an average size of 1000 nm or less. In certain instances, the produced population of liposomes has an average size of 800 nm or less. In certain instances, the produced population of liposomes has an average size of 500 nm or less. In certain instances, the produced population of liposomes has an average size of 400 nm or less. In certain instances, the produced population of liposomes has an average size of 300 nm or less. In certain instances, the produced population of liposomes has an average size of 250 nm or less. In certain instances, the produced population of liposomes has an average size of 200 nm or less. In certain instances, the produced population of liposomes has an average size of 100 nm or less. In certain instances, the produced population of liposomes has an average size of 50 nm or less. For example, the produced population of liposomes may include small unilamellar vesicles (SUVs), e.g., unilamellar vesicles having an average size of 100 nm or less, such as ranging from 10 nm to 100 nm.

In order to produce the population of liposomes, methods of the present disclosure involve the use of a liposome extrusion device as described herein. As described above, in certain embodiments, the membrane of the liposome extrusion device is a porous membrane and the method includes passing the suspension of liposomes (e.g., a heterogeneous population of liposomes) through the porous membrane to produce a population of liposomes (e.g., a population of liposomes having a defined size). In certain embodiments, passing the suspension of liposomes through the membrane includes applying a force on the suspension of liposomes such that the liposomes traverse from one side of the membrane to the other side of the membrane. As the liposomes traverse the membrane, the liposomes pass through the pores in the porous membrane to produce the population of liposomes. The embodiments of the method include extruding a population of liposomes from the porous membrane. In certain instances, the starting suspension of liposomes has an average size that is larger than the pores of the membrane. In some instances, passing larger-sized liposomes through smaller-sized pores in the membrane resizes the liposomes to an average size approximately the same as the size of the pores of the membrane. Thus, in certain cases, passing the liposomes through the membrane produces a population of liposomes (e.g., a population of liposomes having a defined size).

In some instances, applying a force on the suspension of liposomes includes applying a centrifugal force to the suspension of liposomes in a manner sufficient to pass the liposomes through the membrane to produce a population of liposomes. For example, the method may include the use of a centrifuge, where the liposome extrusion device containing the suspension of liposomes is placed in the centrifuge and the centrifuge is operated in a manner sufficient to apply a centrifugal force on the suspension of liposomes. The centrifugal force may be applied to the suspension of liposomes such that the liposomes are forced through the pores of the membrane as described above, thus extruding a population of liposomes from the membrane. As such, in some cases, the method includes spinning the suspension of liposomes in a centrifuge. The suspension of liposomes may be contained in a liposome extrusion device containing the membrane, and thus the method may include spinning the liposome extrusion device containing the suspension of liposomes in a centrifuge such that the liposomes are forced through the pores of the membrane as described above.

In certain embodiments, applying the centrifugal force results in positioning the population of liposomes in one of the liquid containers. For example, as described above, applying the centrifugal force results in the suspension of liposomes traversing from one liquid container into the other liquid container, and thus applying the centrifugal force positions the suspension of liposomes in the liquid container opposing the liquid container the suspension of liposomes was initially contained in. As such, applying the centrifugal force may include positioning the liposome extrusion device in a centrifuge such that a liquid container containing the suspension of liposomes is positioned proximal (e.g., closer) to the axis of rotation of the centrifuge and an opposing liquid container is positioned distal (e.g., further away) from the axis of rotation. When the centrifugal force is applied (e.g., by spinning the liposome extrusion device in the centrifuge) the centrifugal force is applied to the suspension of liposomes to force the suspension of liposomes from the proximal liquid container into the distal liquid container, thus traversing the membrane between the liquid containers.

Some embodiments of the subject methods include applying the centrifugal force to the suspension of liposomes a single time in a manner sufficient to pass the liposomes through the membrane to produce a population of liposomes. In certain embodiments, the method for producing a population of liposomes includes repeating the application of the centrifugal force one or more times. As such, certain embodiments of the method include methods where applying the centrifugal force is repeated one or more times to produce the population of liposomes. For example, applying the centrifugal force may be repeated 1 or more times, such as 2 or more times, or 3 or more times, or 4 or more times, or 5 or more times, or 6 or more times, or 7 or more times, or 8 or more times, or 9 or more times, or 10 or more times, including 15 or more times, or 20 or more times, or 25 or more times. As such, certain embodiments of the method include passing the suspension of liposomes through the porous membrane one or more times to produce a population of liposomes. For instance, certain embodiments of the method include passing the suspension of liposomes through the porous membrane 1 or more times, such as 2 or more times, or 3 or more times, or 4 or more times, or 5 or more times, or 6 or more times, or 7 or more times, or 8 or more times, or 9 or more times, or 10 or more times, including 15 or more times, or 20 or more times, or 25 or more times to produce a population of liposomes (e.g., a population of liposomes having a defined size).

As described above, when applying the centrifugal force, the liposome extrusion device is positioned in the centrifuge such that the liquid container containing the suspension of liposomes is positioned proximal (e.g., closer) to the axis of rotation of the centrifuge and the opposing liquid container is positioned distal (e.g., further away) from the axis of rotation. Thus, in embodiments where applying the centrifugal force is repeated one or more times, the method may include inverting the liposome extrusion device after applying the centrifugal force, such that the liposome extrusion device is inverted before applying the next centrifugal force. In some cases, the method includes inverting the liposome extrusion device between each repetition of applying the centrifugal force. In certain instances, inverting the liposome extrusion device includes inverting the position of the liposome extrusion device in the centrifuge. In certain instances, inverting the liposome extrusion device includes inverting the orientation of the liposome extrusion device in the centrifuge. For example, inverting the position of the liposome extrusion device in the centrifuge may include removing the liposome extrusion device from the centrifuge and inserting the liposome extrusion device back into the centrifuge in an orientation opposite from the orientation of the liposome extrusion device before the liposome extrusion device was removed from the centrifuge. For instance, the liposome extrusion device may initially contain the suspension of liposomes in the first liquid container and be positioned in the centrifuge with the first liquid container proximal (e.g., closer) to the axis of rotation of the centrifuge and the opposing second liquid container positioned distal (e.g., further away) from the axis of rotation of the centrifuge. Upon application of the centrifugal force, as described above, the suspension of liposomes traverses from the first liquid container to the second liquid container such that the suspension of liposomes is extruded from the first liquid container into the second liquid container through the membrane. As such, the suspension of liposomes will be contained in the second liquid container. The liposome extrusion device may then be inverted, for example by removing the liposome extrusion device from the centrifuge and reinserting the liposome extrusion device into the centrifuge in an opposite orientation, such that the second liquid container (e.g., the liquid container now containing the suspension of liposomes) is positioned in the centrifuge proximal (e.g., closer) to the axis of rotation of the centrifuge and the opposing first liquid container is positioned distal (e.g., further away) from the axis of rotation of the centrifuge. Application of the centrifugal force would then cause the suspension of liposomes to be extruded from the second liquid container into the first liquid container through the membrane, such that the suspension of liposomes is contained in the first liquid container. Repeated alternations of applying the centrifugal force and inverting the liposome extrusion device in the centrifuge can be performed to produce a desired population of liposomes (e.g., a population of liposomes having a defined size).

In certain embodiments, applying a centrifugal force to the suspension of liposomes includes applying a centrifugal force sufficient to cause the liposomes to pass through the pores of the membrane. In some cases, the applied centrifugal force is greater than standard gravity, such as for example 2 g or more, or 5 g or more, or 10 g or more, or 25 g or more, or 50 g or more, or 100 g or more, or 250 g or more, or 500 g or more, or 750 g or more, or 1000 g or more, or 1500 g or more, or 2000 g or more, or 2500 g or more, or 3000 g or more, or 3500 g or more, or 4000 g or more, or 4500 g or more, or 5000 g or more, or 5500 g or more, or 6000 g or more, or 6500 g or more, or 7000 g or more, or 7500 g or more, or 8000 g or more, or 8500 g or more, or 9000 g or more, or 9500 g or more, or 10,000 g or more.

As described above, in some cases, applying a centrifugal force includes spinning the liposome extrusion device containing the suspension of liposomes in a centrifuge, and thus in these embodiments, applying a sufficient centrifugal force may include spinning at 10 rpm or more, such as 50 rpm or more, or 100 rpm or more, or 250 rpm or more, or 500 rpm or more, or 750 rpm or more, or 1000 rpm or more, or 1500 rpm or more, or 2000 rpm or more, or 2500 rpm or more, or 3000 rpm or more, or 3500 rpm or more, or 4000 rpm or more, or 4500 rpm or more, or 5000 rpm or more, or 5500 rpm or more, or 6000 rpm or more, or 6500 rpm or more, or 7000 rpm or more, or 7500 rpm or more, or 8000 rpm or more, or 8500 rpm or more, or 9000 rpm or more, or 9500 rpm or more, or 10,000 rpm or more.

In some instances, the centrifugal force is applied for a certain amount of time. The amount of time the centrifugal force is applied may be a time equal to or greater than the time needed for the suspension of liposomes to pass through the pores of the membrane at the applied centrifugal force. For example, the method may include applying a centrifugal force for a time such as 1 min or more, or 2 min or more, or 3 min or more, or 4 min or more, or 5 min or more, or 6 min or more, or 7 min or more, or 8 min or more, or 10 min or more. In some cases, the method may include applying a centrifugal force for a time such as 10 min or less, or 9 min or less, or 8 min or less, or 7 min or less, or 6 min or less, or 5 min or less, or 4 min or less, or 3 min or less, or 2 min or less, or 1 min or less.

In certain embodiments, because a centrifugal force is applied to cause the liposomes to traverse the porous membrane, the methods of the present disclosure may be performed at atmospheric pressure. In some cases, the subject method includes applying the centrifugal force at atmospheric pressure. For example, methods of the present disclosure may not require a pressure greater than atmospheric pressure to be applied to the suspension of liposomes. In some cases, using methods of the present disclosure, a population of liposomes is produced at standard atmospheric pressure. Thus, certain embodiments of the subject methods do not include applying a pressure on the suspension of liposomes, e.g., either manually or by increasing the pressure of a gas or liquid contacting the suspension of liposomes.

In certain embodiments, the method includes sealing the liposome extrusion device prior to applying the centrifugal force. Sealing the liposome extrusion device may facilitate retention of the suspension of liposomes inside the liposome extrusion device while the centrifugal force is being applied. For example, as described above, the method may include connecting the membrane component to the first liquid container and the second liquid container. In some cases, connecting the membrane component to the first liquid container may facilitate the production of a seal, such as a substantially liquid-tight and/or substantially gas-tight seal, between the first liquid container and the membrane component. In some cases, connecting the membrane component to the second liquid container may facilitate the production of a seal, such as a substantially liquid-tight and/or substantially gas-tight seal, between the second liquid container and the membrane component. As such, the liposome extrusion device, and each component thereof (e.g., first liquid container, second liquid container and membrane component), may be substantially liquid-tight and/or substantially gas-tight. By "liquid-tight" is meant that a liquid contained inside the liposome extrusion device does not substantially leak out of the liposome extrusion device and that a liquid outside the liposome extrusion device does not substantially enter into the liposome extrusion device. By "gas-tight" is meant that a gas contained inside the liposome extrusion device does not substantially leak out of the liposome extrusion device and that a gas outside the liposome extrusion device does not substantially enter into the liposome extrusion device. Thus, in certain embodiments, the liposome extrusion device is a sealed liposome extrusion device, such as a liquid-tight and/or gas-tight liposome extrusion device. As such, an interior of the liposome extrusion device may be sealed from the surrounding atmosphere. For example, the interior of the first liquid container, the interior of the second liquid container and the interior of the membrane component may be sealed from the surrounding atmosphere. In some instances, the method may include unsealing the liposome extrusion device prior to introducing a volume of the suspension of liposomes into the liposome extrusion device. Unsealing the liposome extrusion device may expose the contents of the liposome extrusion device to the surrounding environment and allow access to the interior volume of the liposome extrusion device. Thus, a user that has access to the interior volume of the liposome extrusion device may introduce the volume of the suspension of liposomes into the liposome extrusion device for producing the population of liposomes as described above. In some cases, unsealing the liposome extrusion device includes disconnecting the first liquid container from the membrane component to expose the interior of the first liquid container. In some cases, unsealing the liposome extrusion device includes disconnecting the second liquid container from the membrane component to expose the interior of the second liquid container.

In certain embodiments, the method also includes mixing the contents of the liposome extrusion device after introducing the suspension of liposomes into the liposome extrusion device. The mixing may be performed using any convenient protocol. For example, the mixing may be performed using an agitator. The agitator may be any convenient agitator sufficient for mixing a liquid inside a liquid container, including, but not limited to, vortexers, sonicators, shakers (e.g., manual, mechanical, or electrically powered shakers), rockers, oscillating plates, magnetic stirrers, static mixers, rotators, blenders, mixers, tumblers, orbital shakers, among other agitating protocols.

In some cases, the method also includes assaying the produced population of liposomes. Assaying the population of liposomes may be performed using any suitable assay apparatus. For example, the assay may be an assay for determining the average size of the population of liposomes, the polydispersity of the population of liposomes, or a combination thereof. In some cases, the assay may be performed by dynamic light scattering (DLS). In some cases, the assay apparatus may be a flow cytometer. In these embodiments, the assaying includes flow cytometrically analyzing the population of liposomes. In certain embodiments, the liposomes include a fluorescent label, and thus certain embodiments of the assaying include contacting the population of liposomes with electromagnetic radiation (e.g., light), such as electromagnetic radiation having a wavelength that corresponds to an excitation maxima of the fluorescent label of the liposomes. The assaying may further include detecting emitted light from the excited fluorescent label. For instance, the method may include detecting emitted light from the excited fluorescent label at one or more wavelengths that correspond to the emission maxima of the fluorescent label. In certain embodiments, the population of liposomes may be used in methods for calibrating a flow cytometer, e.g., the population of liposomes may be used as a calibration standard for a flow cytometer.

In certain embodiments, the fluorescent label includes one or more detectable moieties or markers that are detectible based on, for example, fluorescence emission maxima, fluorescence polarization, fluorescence lifetime, light scatter, mass, molecular mass, or combinations thereof. In certain embodiments, the fluorescent label includes a fluorophore (i.e., a fluorescent label, fluorescent dye, etc.). Fluorophores of interest may include but are not limited to dyes suitable for use in analytical applications (e.g., flow cytometry, imaging, etc.). A large number of dyes (e.g., non-polymeric dyes) are commercially available from a variety of sources, such as, for example, Molecular Probes (Eugene, Oreg.) and Exciton (Dayton, Ohio). For example, the fluorophore of the dye may be 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin (PE); o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; carotenoid-protein complexes, such as peridinin-chlorophyll proteins (PerCP); allophycocyanin (APC); or combinations thereof.

Suitable flow cytometry systems and methods for analyzing samples that may be employed in methods of the invention include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49(pt 1):17-28; Linden, et. al., *Semin Thromb Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ and FACSCanto II™ flow cytometers, BD Biosciences FACSVantage™, BD Biosciences FACSort™, BD Biosciences FACSCount™, BD Biosciences FACSScan™, and BD Biosciences FACSCalibur™ systems, BD Biosciences Influx™ cell sorter, BD Biosciences Accuri™ C6 flow cytometer; BD Biosciences LSR-Fortessa™ flow cytometer, BD Biosciences LSRFortessa™ X-20 flow cytometer, BD Biosciences FACSVerse™ flow cytometer, BD Biosciences FACSAria™ III and BD FACSAria™ Fusion flow cytometers, BD Biosciences FAC-SJazz™ flow cytometer, or the like. In certain embodiments, the subject systems are flow cytometric systems, such those described in U.S. Pat. Nos. 3,960,449; 4,347,935; 4,667, 830; 5,245,318; 5,464,581; 5,483,469; 5,602,039; 5,643, 796; 5,700,692; 6,372,506 and 6,809,804, the disclosures of which are herein incorporated by reference in their entirety.

Other methods of analysis may also be used, such as, but not limited to, liquid chromatography-mass spectrometry or gas chromatography-mass spectrometry systems. For example, assaying may include the use of an analytical separation device such as a liquid chromatograph (LC), including a high performance liquid chromatograph (HPLC), a micro- or nano-liquid chromatograph or an ultra-high pressure liquid chromatograph (UHPLC) device, a capillary electrophoresis (CE), or a capillary electrophoresis chromatograph (CEC) apparatus. Mass spectrometer (MS) systems may also be used to assay the dye compositions. Examples of mass spectrometers may include, but are not limited to, electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof.

In certain embodiments, the method also includes storing the liposomes for a period of time. The liposomes may be stored for a period of time before and/or after producing the population of liposomes. In some instances, the liposomes are stored for a period of time such as 1 hour or more, or 4 hours or more, or 6 hours or more, or 12 hours or more, or 18 hours or more, or 24 hours or more, or 48 hours or more, or 72 hours or more, or 4 days or more, or 5 days or more, or 6 days or more, or 1 week or more.

Embodiments of the method may further include shipping the liposomes to a remote location. A "remote location," is a location other than the location at which the liposomes are produced. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or one hundred miles or more apart.

Liposome Extrusion Devices

Aspects of the present disclosure include liposome extrusion devices. A liposome extrusion device of the present disclosure is useful for the production of a population of liposomes. Liposome extrusion devices according to certain embodiments of the present disclosure include a porous membrane and a component configured to position the membrane between a first liquid container and a second liquid container. In some instances, when the component is attached to the first liquid container and the second liquid container, an interior of the liposome extrusion device is sealed from the surrounding atmosphere. For example, an interior of the first liquid container, an interior of the second liquid container and an interior of the component may be sealed from the surrounding atmosphere. Further aspects of each of the elements of the liposome extrusion device are described in more detail below.

As indicated above, the liposome extrusion device includes a porous membrane. A porous membrane is a membrane that includes a plurality of pores in the membrane. The pores may be pores that have defined pore sizes. The size of a pore may be measured as a dimension of the opening of the pore, such as the largest dimension of the opening of the pore. For example, in some cases, the pore is an opening in the membrane having a substantially circular cross section. Thus, in these cases, the pore size can be measured as the diameter of the pore. For instance, the pores in the membrane may have a pore size (e.g., an average pore size) of 1000 nm or less, such as 900 nm or less, or 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 20 nm or less, or 15 nm or less, or 10 nm or less, or 5 nm or less, or 1 nm or less. In certain instances, the membrane pores have an average pore size of 1000 nm or less. In certain instances, the membrane pores have an average pore size of 900 nm or less. In certain instances, the membrane pores have an average pore size of 800 nm or less. In certain instances, the membrane pores have an average pore size of 700 nm or less. In certain instances, the membrane pores have an average pore size of 600 nm or less. In certain instances, the membrane pores have an average pore size of 500 nm or less. In certain instances, the membrane pores have an average pore size of 400 nm or less. In certain instances, the membrane pores have an average pore size of 300 nm or less. In certain instances, the membrane pores have an average pore size of 250 nm or less. In certain instances, the membrane pores have an average pore size of 200 nm or less. In certain instances, the membrane pores have an average pore size of 150 nm or less. In certain instances, the membrane pores have an average pore size of 100 nm or less. In certain instances, the membrane pores have an average pore size of 75 nm or less. In certain instances, the membrane pores have an average pore size of 50 nm or less. In certain instances, the membrane pores have an average pore size of 25 nm or less. In certain instances, the membrane pores have an average pore size of 20 nm or less. In certain instances, the membrane pores have an average pore size of 15 nm or less. In certain instances, the membrane pores have an average pore size of 10 nm or less. In certain instances, the membrane pores have an average pore size of 5 nm or less. In certain instances, the membrane pores have an average pore size of 1 nm or less. In some embodiments, the pores in the membrane are substantially the same size. Stated another way, the pores in the membrane may be uniform in size. A porous membrane that includes uniformly sized pores may facilitate the production of a population of liposomes having a defined size.

In certain embodiments, the membrane pores pass through the membrane in a non-tortuous path. For example, the porous membrane may include pores having a longitudinal axis substantially perpendicular to a surface of the membrane. In some cases, the porous membrane may include pores having a longitudinal axis at an angle of less than 90° relative to a surface of the membrane. In certain instances, the porous membrane does not include a web-like or matrix construction where a network of pores are interconnected, thus forming a tortuous path through the membrane. Stated another way, the porous membrane may include distinct pores that pass through the membrane without intersecting other pores in the membrane.

In certain embodiments, the porous membrane is composed of one or more layers of a membrane material. For example, the membrane may be composed of a single layer of a membrane material. In other embodiments, the membrane is composed of two or more layers of a membrane material. For instance, the membrane may include 2 layers of a membrane material, such as 3 or more layers, or 4 or more layers, or 5 or more layers, or 6 or more layers, or 7 or more layers, or 8 or more layers, or 9 or more layers, or 10 or more layers of a membrane material. In some cases, the membrane includes 2 layers of a membrane material. In some cases, the membrane includes 3 layers of a membrane material. In embodiments that include two or more layers of a membrane material, the membrane material of each layer may be the same, or may be different. In certain embodiments, the pore size of each of the two or more layers of the membrane material is the same. In other embodiments, the pore size of at least two of the two or more layers of the membrane material are different.

The membrane may be composed of any suitable membrane material. In some cases, the membrane material is compatible with the liquid and/or liposomes in contact with the membrane. For example, the membrane material can be a liquid-compatible membrane material, such as a hydrophilic membrane material. In some cases, the liposomes may be in an aqueous liquid, and in these cases, the membrane material may be compatible with aqueous media. By "compatible" is meant that the membrane material is substantially inert (e.g., does not significantly react with or degrade) in the presence of the liquid and/or liposomes or other ingredients in contact with the membrane. Examples of suitable membrane materials include polymeric materials, for example, polymers, such as, but not limited to, polycarbonate, polyester, nylon, cellulose, cellulose acetate, polyethylene terephthalate, and the like. In some instances, the membrane material is polycarbonate. In some instances, the membrane material is polyester.

Embodiments if the subject liposome extrusion devices also include a component configured to position the membrane between a first liquid container and a second liquid container. The component configured to position the membrane between the first liquid container and the second liquid container may also be referred to as a membrane component or a membrane support herein. In some instances, the membrane component supports the membrane in a position between a first liquid container and a second liquid container. The membrane may be substantially planar, e.g., where the suspension of liposomes traverses the membrane in a direction orthogonal to the planar surface of the membrane. In some cases, the component positions the membrane between the first liquid container and the second liquid container such that the plane of the membrane is transverse to a longitudinal axis of the component. For instance, the longitudinal axis of the component may be perpendicular to the plane of the membrane. In some instances, the longitudinal axis of the component is aligned with the longitudinal axis of the first liquid container and the longitudinal axis of the second liquid container. As such, the component may be configured to position the membrane between the first liquid container and the second liquid container such that the plane of the membrane is transverse to a longitudinal axis of the first liquid container and transverse to a longitudinal axis of the second liquid container.

In certain embodiments, the component is configured such that the membrane is positioned between a first end of the component and a second end of the component. The first end of the component may be an open end, for example that connects to an open end of the first liquid container. The second end of the component may be an open end, for example that connects to an open end of the second liquid container.

In some cases, the component may be a single unit. In these embodiments, the membrane may be supported and positioned within the single unit of the component. In other embodiments, the component may include two or more subcomponents, such as a first subcomponent and a second subcomponent. The first subcomponent and the second subcomponent may be removably attached to each other, such that the first subcomponent is removably attached to the second subcomponent, and the second subcomponent is removably attached to the first subcomponent. In some instances, the membrane is positioned at an interface between the first subcomponent and the second subcomponent. The interface between the first subcomponent and the second subcomponent may include a surface having one or more holes allowing fluid communication from the first fluid container through the component to the second fluid container. In some cases, the interface includes a first surface as part of the first subcomponent and a second surface as part of the second subcomponent, with the membrane positioned between the first surface and the second surface. Removable attachment of the first subcomponent and the second subcomponent facilities access to the membrane, such as for example allowing the membrane to be replaced with another membrane. In some cases, the component includes an intra-component connector that connects the first subcomponent to the second subcomponent. The intra-component connector can be any suitable connector, such as, but not limited to screw threads, clips, snaps, pressure fittings, and the like. For instance, in some cases, the first subcomponent includes an intra-component connector, such as screw threads, on the end of the first subcomponent that attaches to the second subcomponent, and the second subcomponent includes an intra-component connector, such as corresponding screw threads, on the end of the second subcomponent that attaches to the first subcomponent.

In certain embodiments, the membrane component may include a first end and a second end opposing the first end. In some embodiments, the first end includes a first opening. In some instances, the first opening in the membrane component exposes a first surface of the membrane. In some embodiments, the second end of the membrane component includes a second opening. In some instances, the second opening in the membrane component exposes a second (opposing) surface of the membrane. The membrane component may further include one or more side walls, which form the sides of the membrane component between the opening at the first end of the membrane component and the opening at the opposing second end of the membrane component. In some instances, there are substantially no gaps between the membrane and the side wall(s) of the membrane component, such that the membrane forms a liquid-tight seal against the side wall(s) of the membrane component. As such, liquid and/or liposomes traversing the membrane may only pass through the pores in the membrane. In certain embodiments, the membrane component is in the shape of a cylinder, where the cylinder has a first opening at a first end and a second opening at a second opposing end of the cylinder. In some cases, the membrane component has a circular cross section. As such, the membrane may also have a circular shape.

As described above, the component may be connected to the first liquid container and the second liquid container. As such, in certain embodiments, the component includes a first connector for connecting the component to the first liquid container, and a second connector for connecting the component to the second liquid container. The first connector and the second connector may be positioned on opposing ends of the component. The first and second connectors can be any suitable connectors, such as, but not limited to screw threads, clips, snaps, pressure fittings, and the like. For instance, in some cases, the component includes a first connector, such as screw threads, on the end of the component that attaches to the first liquid container, and the first liquid container includes a corresponding connector, such as corresponding screw threads, on the end of the first liquid container that attaches to the first connector of the component. In addition, the component may include a second connector, such as screw threads, on the end of the component that attaches to the second liquid container, and the second liquid container may include a corresponding connector, such as corresponding screw threads, on the end of the second liquid container that attaches to the second connector of the component.

As described above, the membrane component may be configured as a flow path through which a volume of a fluid (e.g., gas or liquid) can flow through as the fluid traverses from the first liquid container to the second liquid container or from the second liquid container to the first liquid container. For example, the membrane component may be configured as a flow path for a liquid, such as a suspension of liposomes. The size of the membrane component, and thus the interior volume of the membrane component may range from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 2 ml, or 0.1 ml to 1.5 ml, or 0.1 ml to 1 ml, or 0.1 ml to 0.5 ml. In certain instances, the membrane component is configured to have an interior volume ranging from 0.1 ml to 5 ml, such as, for example, 0.5 ml, or 1 ml, or 1.5 ml, or 2 ml. In other instances, the membrane component is configured to have an interior volume ranging from 0.1 ml to 100 ml, such as 50 ml, or 25 ml.

In certain embodiments, the membrane component has a width (which may also be referred to as the diameter for cylindrical membrane components) that is the same or substantially the same as the width or diameter of the first liquid container and/or the second liquid container. For instance, the membrane component may have an inner diameter the same or substantially the same as an inner diameter of the first liquid container and/or the second liquid container. In some cases, the membrane component has a width (or diameter) ranging from 0.5 cm to 5 cm, such as 0.5 cm to 4.5 cm, or 0.5 cm to 4 cm, or 0.5 cm to 3.5 cm, or 0.5 cm to 3 cm, or 0.5 cm to 2.5 cm, or 0.5 cm to 2 cm, or 0.5 cm to 1.5 cm, or 0.5 cm to 1 cm. In some instances, the membrane component has a width (or diameter) ranging from 0.5 cm to 2.5 cm. In some instances, the membrane component has a width (or diameter) ranging from 0.5 cm to 1 cm. In certain embodiments, the membrane component has a length ranging from 1 cm to 20 cm, such as 1 cm to 15 cm, or 1 cm to 10 cm, or 1 cm to 5 cm, or 1 cm to 2.5 cm. In some instances, the membrane component has a length ranging from 1 cm to 10 cm. In some instances, the membrane component has a length ranging from 1 cm to 5 cm. In some instances, the membrane component has a length ranging from 1 cm to 2.5 cm.

Embodiments of the membrane component can be compatible with the liquid and/or liposomes or other ingredients that may be in contact with the membrane component. Examples of suitable membrane component materials for the liposome extrusion devices include, but are not limited to, plastics, such as polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), and the like.

As discussed above, in certain embodiments, the membrane component is configured to position the membrane between a first liquid container and a second liquid container. As such, in some instances, the liposome extrusion device includes the first liquid container and the second liquid container. Embodiments of the subject liquid containers may be configured to contain a volume of a liquid (e.g., a suspension of liposomes and/or population of liposomes). In some instances, the subject liquid container includes a first end and a second end opposing the first end. In some embodiments, the first end includes an opening. In these instances, the opening in the liquid container exposes the interior of the liquid container to the surrounding environment, e.g., such that the contents of the liquid container are under the same atmospheric pressure as the surrounding environment. For example, the opening may be used to allow access to the interior of the liquid container, such as for introducing a suspension of liposomes into the liquid container or removing a suspension of liposomes from the liquid container. In certain instances, the membrane component is removable from the first and/or second liquid container, such that after applying a centrifugal force in a manner sufficient to pass the liposomes through the membrane, the membrane component may be removed from the first and/or second liquid container. In these instances, a removable membrane component allows access to the liposomes that have passed through the membrane. These liposomes may be collected and analyzed or used in subsequent procedures.

In some instances, the liquid container (e.g., the first and/or second liquid container) includes a closed end opposite from the open end of the liquid container. As such, the liquid container may be configured to contain a volume of liquid as described above. The size of the liquid container may depend on the volume of liquid to be held in the liquid container. For instance, the liquid container may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 2 ml, or 0.1 ml to 1.5 ml, or 0.1 ml to 1 ml, or 0.1 ml to 0.5 ml. In certain instances, the liquid container is configured to hold a volume ranging from 0.1 ml to 5 ml, such as, for example, 0.5 ml, or 1 ml, or 1.5 ml, or 2 ml. In other instances, the liquid container is configured to hold a volume ranging from 0.1 ml to 100 ml, such as 50 ml, or 25 ml.

The liquid container (e.g., the first and/or second liquid container) may further include one or more side walls, which form the sides of the liquid container between the opening at the first end of the liquid container and the closed second end of the liquid container. In certain embodiments, the liquid container is in the shape of a cylinder, where the cylinder has an opening at a first end and a closed second opposing end of the cylinder. In some cases, the liquid container has a circular cross section. The shape of the liquid container may vary and may depend on the use of the liposome extrusion device. For example, the liquid container may be configured in a shape that is compatible with the methods of the present disclosure. For instance, the liquid container may be configured in a shape compatible with typical laboratory equipment used to perform the method, such as a shape compatible with a centrifuge. As described above, the liquid container may be configured to hold a volume of a liquid. In these embodiments, the liquid container may be a vial or a test tube. In certain cases, the liquid container is a vial. In certain cases, the liquid container is a test tube. Examples of suitable liquid containers include, but are not limited to, centrifuge tubes, microcentrifuge tubes, Eppendorf® tubes, and the like.

In certain embodiments, the liquid container (e.g., the first and/or second liquid container) has a width (which may also be referred to as the diameter for cylindrical liquid containers) ranging from 0.5 cm to 5 cm, such as 0.5 cm to 4.5 cm, or 0.5 cm to 4 cm, or 0.5 cm to 3.5 cm, or 0.5 cm to 3 cm, or 0.5 cm to 2.5 cm, or 0.5 cm to 2 cm, or 0.5 cm to 1.5 cm, or 0.5 cm to 1 cm. In some instances, the liquid container has a width (or diameter) ranging from 0.5 cm to 2.5 cm. In some instances, the liquid container has a width (or diameter) ranging from 0.5 cm to 1 cm. In certain embodiments, the liquid container has a length ranging from 1 cm to 20 cm, such as 1 cm to 15 cm, or 1 cm to 10 cm, or 1 cm to 5 cm, or 1 cm to 2.5 cm. In some instances, the liquid container has a length ranging from 1 cm to 10 cm. In some instances, the liquid container has a length ranging from 1 cm to 5 cm. In some instances, the liquid container has a length ranging from 1 cm to 2.5 cm.

Embodiments of the liquid container (e.g., the first and/or second liquid container) can be compatible with the liquid and/or liposomes or other ingredients that may be in contact with the liquid container. Examples of suitable liquid container materials for the liposome extrusion devices include, but are not limited to, plastics, such as polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), and the like.

In some embodiments, as described above, the liquid container (e.g., the first and/or second liquid container) is configured as a container, where the container is configured to hold a certain volume of a liquid. In some embodiments, the liquid container may be a sealable container. That is, the liquid container may include a seal or a sealable surface that substantially prevents the contents of the liquid container (e.g., liquid inside the liquid container) from exiting the liquid container. The seal or sealable surface of the liquid container may also substantially prevent other substances from entering the liquid container. For example, the seal or sealable surface may be a liquid-tight, such as a water-tight, seal that substantially prevents liquids, such as water or aqueous solutions or suspensions, from entering or exiting the liquid container, or may be a gas-tight seal, such as an air-tight seal, that substantially prevents gases, such as air, from entering or exiting the liquid container. In some instances, the seal or sealable surface can be unsealed, such that the contents of the liquid container may be exposed to the surrounding environment when so desired, e.g., if it is desired to remove a portion of the contents of the liquid container.

In certain embodiments, the liquid container (e.g., the first and/or second liquid container) includes a sealable surface as described above. The sealable surface may be present on a surface at an open end of the liquid container. For instance, the sealable surface of the liquid container may be a surface on the open end of the liquid container that interfaces with a corresponding seal or sealable surface on the membrane component. In some cases, connection of the liquid container to the membrane component causes the sealable surface of the liquid container to contact and seal against the corresponding seal or sealable surface of the membrane component, thus creating a liquid-tight and/or gas-tight seal between the liquid container and the membrane component. As such, an interior of the liposome extrusion device may be sealed from the surrounding atmosphere. For example, when the membrane component is attached to the first liquid container and the second liquid container, the interior of the first liquid container, the interior of the second liquid container and the interior of the membrane component may be sealed from the surrounding atmosphere. In some cases, when the membrane component is attached to the first liquid container and the second liquid container, the interior of the first liquid container is sealed from the surrounding atmosphere. In some cases, when the membrane component is attached to the first liquid container and the second liquid container, the interior of the second liquid container is sealed from the surrounding atmosphere. In some cases, when the membrane component is attached to the first liquid container and the second liquid container, the interior of the membrane component is sealed from the surrounding atmosphere.

In some instances, the seal is made of a resilient material to provide a barrier (e.g., liquid-tight seal and/or gas-tight seal) for retaining the contents of the liquid container inside the liquid container. Particular types of seals include, but are not limited to, films, such as polymer films, caps, etc., depending on the type of container. Suitable materials for the seal include, for example, rubber or polymer seals, such as, but not limited to, silicone rubber, natural rubber, styrene butadiene rubber, ethylene-propylene copolymers, polychloroprene, polyacrylate, polybutadiene, polyurethane, styrene butadiene, and the like, and combinations thereof. The seal may be present at the open end of the liquid container that interfaces with a corresponding seal or sealable surface on the membrane component. In some cases, connection of the liquid container to the membrane component causes the seal of the liquid container to contact and seal against the corresponding seal or sealable surface of the membrane component, thus creating a liquid-tight and/or gas-tight seal between the liquid container and the membrane component. In some cases, the seal is in the shape of an O-ring having a diameter the same or substantially the same as the diameter of the liquid container and/or the membrane component. As such, an interior of the liposome extrusion device may be sealed from the surrounding atmosphere. For example, when the membrane component is attached to the first liquid container and the second liquid container, the interior of the first liquid container, the interior of the second liquid container and the interior of the membrane component may be sealed from the surrounding atmosphere.

As described above, certain embodiments of the liposome extrusion device include a porous membrane that includes one or more layers of a membrane material as described herein. The liposome extrusion device may also include a component configured to position the membrane between the first liquid container and the second liquid container.

An example of a liposome extrusion device according to embodiments of the present disclosure is shown in FIG. 1. In FIG. 1, the liposome extrusion device 5 is shown in four views: FIG. 1, panel A, shows an exploded perspective view of the liposome extrusion device; FIG. 1, panel B, shows an exploded cross-sectional view of the liposome extrusion device; FIG. 1, panel C, shown a perspective view of an assembled liposome extrusion device; and FIG. 1, panel D, shows a cross-sectional view of the assembled liposome extrusion device. In FIG. 1, the liposome extrusion device 5 is configured as a vial. The liposome extrusion device 5 includes a first liquid container 10 in the form of a vial (e.g., an Eppendorf tube), and a second liquid container 30, which is also in the form of a vial (e.g., an Eppendorf tube). The liposome extrusion device 5 also includes a membrane component 20, which has a first subcomponent 21 and a second subcomponent 23. The membrane component 20 also includes a porous membrane 22 positioned at an interface between the first subcomponent 21 and the second subcomponent 23. As shown in FIG. 1, assembly of the liposome extrusion device 5 can be performed by positioning the membrane 22 between the first subcomponent 21 and the second subcomponent 23 and attaching the first subcomponent 21 and the second subcomponent 23 together, such that the membrane 22 is held in position between the first subcomponent 21 and the second subcomponent 23. Either one, or both, the first liquid container 10 or second liquid container 30 can be loaded with a suspension of liposomes, and then the first liquid container 10 and the second liquid container 30 can be connected to the membrane component 20 at opposing ends of the membrane component 20.

After the liposome extrusion device is assembled, the liposome extrusion device may then be placed in a centrifuge. The centrifuge may be operated (e.g., by spinning) to apply a centrifugal force to the liposome extrusion device such that the suspension of liposomes from one of the liquid containers passes through the porous membrane 20 and into the opposing liquid container. Extrusion of the liposomes through the pores of the membrane may produce a population of liposomes having a defined size, as described herein.

Systems

Systems of the present disclosure include a liposome extrusion device as described herein. For example, the liposome extrusion device may include a porous membrane and a component (e.g., membrane component) configured to position the membrane between a first liquid container and a second liquid container. As described herein, when the component is attached to the first liquid container and the second liquid container, an interior of the component may be sealed from the surrounding atmosphere. In addition, systems of the present disclosure may also include the first liquid container and the second liquid container, as described herein.

In certain embodiments, the liposome extrusion device includes a suspension of liposomes. For example, during use of the liposome extrusion device, a suspension of heterogeneous liposomes may be introduced into either, or both, the first liquid container or the second liquid container. As described herein, a centrifugal force may then be applied to the suspension of liposomes such that the liposomes pass through the porous membrane to produce a population of liposomes, such as a population of liposomes having a defined size. As such, certain embodiments of the systems of the present disclosure may also include a centrifuge. Centrifuges suitable for use in the subject systems include any of the various types of centrifuges. For example, a suitable centrifuge may include a centrifuge configured to apply a centrifugal force to the suspension of liposomes, which may include a centrifuge configured to apply a centrifugal force sufficient to cause the liposomes to pass through the pores of the membrane. In some cases, the centrifuge is configured to apply a centrifugal force greater than standard gravity, such as for example 2 g or more, or 5 g or more, or 10 g or more, or 25 g or more, or 50 g or more, or 100 g or more, or 250 g or more, or 500 g or more, or 750 g or more, or 1000 g or more, or 1500 g or more, or 2000 g or more, or 2500 g or more, or 3000 g or more, or 3500 g or more, or 4000 g or more, or 4500 g or more, or 5000 g or more, or 5500 g or more, or 6000 g or more, or 6500 g or more, or 7000 g or more, or 7500 g or more, or 8000 g or more, or 8500 g or more, or 9000 g or more, or 9500 g or more, or 10,000 g or more, or 15,000 g or more, or 20,000 g or more, or 25,000 g or more, where in some instances the force is 30,000 g or less, such as 27,500 g or less. In some cases, the centrifuge is configured to apply a centrifugal force by spinning at 10 rpm or more, such as 50 rpm or more, or 100 rpm or more, or 250 rpm or more, or 500 rpm or more, or 750 rpm or more, or 1000 rpm or more, or 1500 rpm or more, or 2000 rpm or more, or 2500 rpm or more, or 3000 rpm or more, or 3500 rpm or more, or 4000 rpm or more, or 4500 rpm or more, or 5000 rpm or more, or 5500 rpm or more, or 6000 rpm or more, or 6500 rpm or more, or 7000 rpm or more, or 7500 rpm or more, or 8000 rpm or more, or 8500 rpm or more, or 9000 rpm or more, or 9500 rpm or more, or 10,000 rpm or more.

As described above, a centrifugal force may be applied to the suspension of liposomes using a centrifuge. As such, the liposome extrusion device may be inserted into a centrifuge in order to apply the centrifugal force to a suspension of liposomes contained in the liposome extrusion device. For example, the liposome extrusion device may be inserted into a centrifuge tube holder of the centrifuge, and the liposome extrusion device may be held in the centrifuge tube holder while the centrifugal force is applied, such as by spinning the centrifuge. In certain embodiments, the system includes an adapter configured to contain the liposome extrusion device. The adapter may facilitate insertion and retention of the liposome extrusion device in the centrifuge. For instance, the adapter may facilitate insertion and retention of the liposome extrusion device in the centrifuge tube holder of the centrifuge. In some instances, the centrifuge tube holder may have a circular cross-section; i.e., the centrifuge tube holder may be in the shape of a cylinder. In some cases, the adapter is also in the shape of a cylinder. For example, the adapter may be configured as a cylinder with an outer surface concentric to an interior surface of the centrifuge tube holder of the centrifuge. The liposome extrusion device may be held within an interior of the adapter. In some instances, an interior surface of the adapter is configured to hold the liposome extrusion device such that the liposome extrusion device does not substantially change position inside the adapter. For example, the position of the liposome extrusion device within the adapter may not substantially change during use, such as when the centrifugal force is applied. As such, in certain cases, an interior surface of the adapter has a shape that substantially conforms to an outer surface of the liposome extrusion device. In certain instances, the adapter may be provided in two or more sections or pieces. The interior of the adapter may be exposed by separating the two sections of the adapter, thus allowing the liposome extrusion device to be inserted or removed from the adapter. As such, the two sections of the adapter are removably attached to each other. As described above, the adapter may be in the shape of a cylinder, and as such, in some cases, the adapter is provided in two longitudinal sections, where the adapter is divided into the two longitudinal sections by a plane along the longitudinal axis of the adapter. The dimensions of the adaptor may vary, as desired. In certain instances, the adapter may have a length ranging from 100 to 150 mm. In some embodiments, the adapter may have a width, e.g., a diameter where the adaptor is configured as a cylinder, ranging from 10 to 35 mm. The adapter may have any outer configuration or shape which is dimensioned so that the adaptor may be accommodated by a holder of a centrifuge device, such that the adaptor can be stably positioned in a holder of a centrifuge device, e.g., as illustrated in the embodiment shown in FIG. 2, described below.

Figure 2:
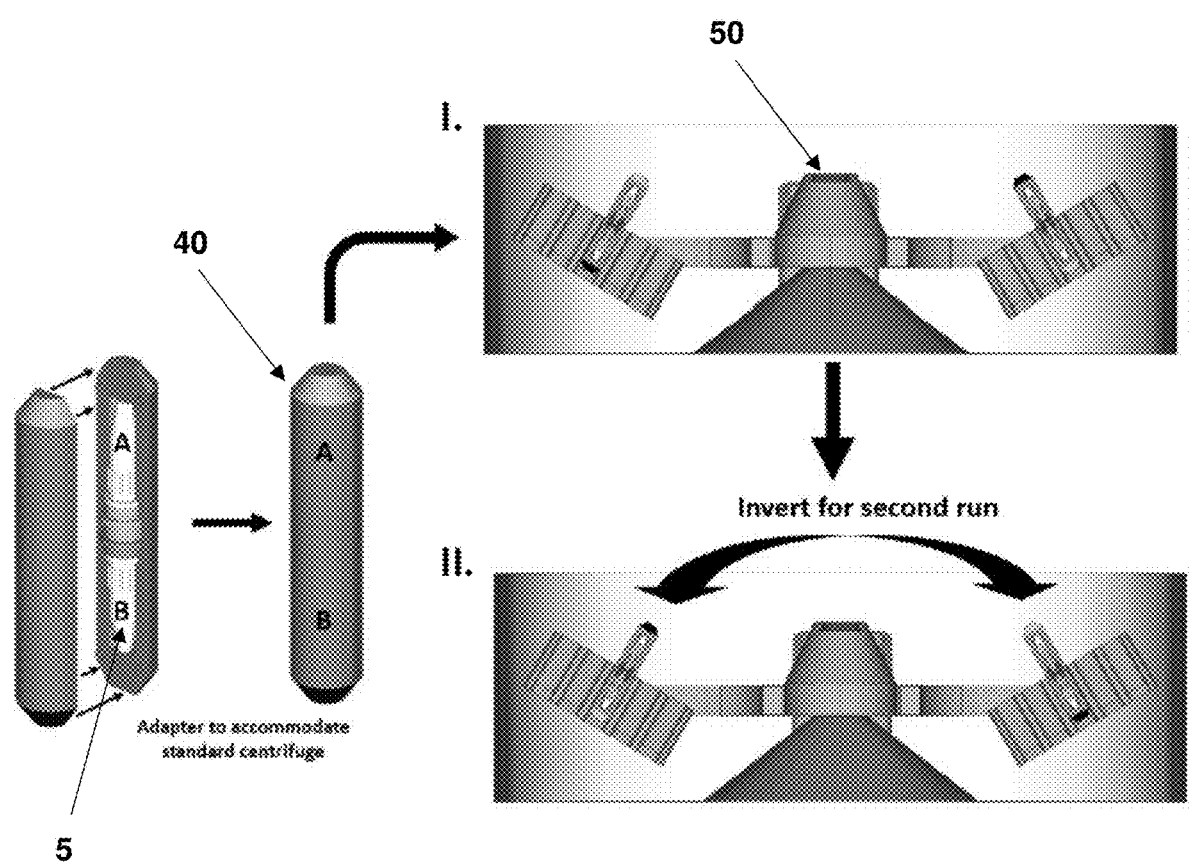
FIG. 2 is an illustration of a system for producing a population of liposomes according to embodiments of the present disclosure.

An example of a system for producing a population of liposomes according to embodiments of the present disclosure is shown in FIG. 2. As shown in FIG. 2, the system includes a liposome extrusion device 5, as described herein. The liposome extrusion device is inserted into an adapter 40, which facilitates insertion and retention of the liposome extrusion device in a centrifuge 50. The liposome extrusion device 5, which is contained in the adapter 40, is inserted into a centrifuge tube holder of the centrifuge 50 and a centrifugal force is applied by spinning the centrifuge. In the embodiment illustrated in FIG. 2, the suspension of liposomes in contained in liquid container A of the liposome extrusion device 5. When applying the centrifugal force, the liposome extrusion device 5 is positioned in the centrifuge 50 such that the liquid container containing the suspension of liposomes A is positioned proximal (e.g., closer) to the axis of rotation of the centrifuge 50 and the opposing liquid container B is positioned distal (e.g., further away) from the axis of rotation. For example, as shown in FIG. 2, liquid container A is positioned at the top and liquid container B is positioned at the bottom of the centrifuge tube holder. When the centrifugal force is applied, the suspension of liposomes traverses from the liquid container A to the liquid container B such that the suspension of liposomes is extruded from the liquid container A into the liquid container B through the membrane (see Step I in FIG. 2). As described herein, the centrifugal force may be applied repeated times. As such, the liposome extrusion device may be inverted after applying the centrifugal force and before applying the next centrifugal force. As shown in FIG. 2 (see Step II), inverting the position of the liposome extrusion device in the centrifuge may be accomplished by removing the liposome extrusion device from the centrifuge and inserting the liposome extrusion device back into the centrifuge in an orientation opposite from the orientation of the liposome extrusion device before the liposome extrusion device was removed from the centrifuge. For instance, after applying the first centrifugal force as described above, the suspension of liposomes in now contained in liquid container B. The liposome extrusion device may be inverted such that liquid container B is positioned proximal (e.g., closer) to the axis of rotation of the centrifuge and the liquid container A is positioned distal (e.g., further away) from the axis of rotation of the centrifuge. For example, as shown in FIG. 2 (Step II), liquid container B is positioned at the top and liquid container A is positioned at the bottom of the centrifuge tube holder. Upon application of the centrifugal force, as described above, the suspension of liposomes traverses from liquid container B to liquid container A such that the suspension of liposomes is extruded from liquid container B into liquid container A through the membrane. Repeated alternations of applying the centrifugal force and inverting the liposome extrusion device in the centrifuge can be performed to produce a desired population of liposomes (e.g., a population of liposomes having a defined size).

Kits

Aspects of the disclosure also include kits that include a subject liposome extrusion device (e.g., a porous membrane and a component (membrane component) as described herein). In certain embodiments, the kit includes a subject liposome extrusion device and a packaging configured to hold the liposome extrusion device. The packaging may be a sealed packaging, e.g., a water-resistant and/or water vapor-resistant container, optionally under a gas-tight and/or vacuum seal. In certain instances, the packaging is a sterile packaging, configured to maintain the device enclosed in the packaging in a sterile environment. By "sterile" is meant that there are substantially no microbes (such as fungi, bacteria, viruses, spore forms, etc.).

In some instances, the kit may also include a first liquid container, such as a centrifuge tube, as described herein. In some instances, the kit may also include a second liquid container, such as a centrifuge tube, as described herein. In some instances, the kit may also include an adapter configured to contain the liposome extrusion device, as described herein.

The kits may further include a liquid. For instance, the kit may include a buffer, such as a sample buffer, a wash buffer, an assay buffer, and the like. In some cases, the kit may include a liquid suitable for a suspension of liposomes. The kits may further include additional reagents, such as but not limited to, detectable labels (e.g., fluorescent labels, colorimetric labels, chemiluminescent labels, multicolor reagents, avidin-streptavidin associated detection reagents, radiolabels, gold particles, magnetic labels, etc.), and the like.

In certain embodiments, the kits may also include a calibration standard. For example, the kits may include a set of labelled beads, such as a set of standard fluorescently labelled beads. The calibration standard may be useful for determining the accuracy of the assay apparatus and for ensuring consistency between subsequent assays. For example, the calibration standard may be useful for determining the accuracy of a flow cytometer. In some cases, the calibration standard includes a labelled bead, such as a fluorescently labelled bead. The fluorescently labelled bead may be a standard fluorescently labeled bead that is typically used as a calibration standard. Examples of standard fluorescently labeled beads include, but are not limited to, fluorescently labelled microparticles or nanoparticles. In some cases, the fluorescently labeled beads are configured such that they remain suspended in the assay mixture and do not substantially settle or aggregate. In some embodiments, the fluorescently labeled beads include, but are not limited to, fluorescently labelled polystyrene beads, fluorescein beads, rhodamine beads, and other beads tagged with a fluorescent dye. Additional examples of fluorescently labeled beads are described in U.S. Pat. Nos. 6,350,619; 7,738,094; and 8,248,597, the disclosures of each of which are herein incorporated by reference in their entirety.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another form would be a computer readable medium, e.g., CD, DVD, Blu-Ray, computer-readable memory (e.g., flash memory), etc., on which the information has been recorded or stored. Yet another form that may be present is a website address which may be used via the Internet to access the information at a removed site. Any convenient form of instructions may be present in the kits.

Utility

The subject methods, devices and systems find use in applications where a population of liposomes of defined size may be desired for research or laboratory testing. In some embodiments, the subject methods, devices and systems facilitate the accurate analysis of analytes (e.g., cells) obtained from a biological sample (e.g., organ, tissue, tissue fragment, fluid). In certain instances, the subject methods, devices and systems find use in testing the accuracy of an apparatus used for the analysis of such analytes for research or laboratory testing. For example, the subject methods, devices and systems find use in testing the accuracy of a flow cytometer. In some cases, the population of liposomes produced using the methods, devices and systems of the present disclosure are used as a calibration standard for an apparatus, such as a flow cytometer. Thus, the subject methods, devices and systems find use in the efficient preparation of a population of liposomes from a suspension of heterogeneous liposomes.

In addition, the subject methods, devices and systems find use in the preparation of a population of liposomes without the need for specialized liposome extrusion systems, such as liposome extrusion systems that require syringes or gas/liquid handling components for applying increased pressure or a vacuum on a suspension of liposomes to force the liposomes through an extrusion membrane. In some instances, the subject methods, devices and systems find use in the production of a population of liposomes using standard laboratory equipment at standard atmospheric pressure. Stated another way, the subject methods, devices and systems find use in the production of a population of liposomes without the application of an increased pressure or a vacuum on a suspension of liposomes.

The subject methods, devices and systems also find use in the preparation of a population of liposomes without the need for opening the liposome extrusion device or exposing the suspension of liposomes to the surrounding atmosphere during the (repeated) centrifugation process, since the liposome extrusion device can be inverted between each application of a centrifugal force. As such, the subject methods, devices and systems facilitate the preparation of a population of liposomes with significantly less or substantially no contamination from contaminants from the surrounding atmosphere or outside environment. In addition, in the event that liposome precipitate forms on the bottom of a liquid container of the liposome extrusion device, the subject methods, devices and systems provide for re-suspension of the precipitate by vortexing the liposome extrusion device without the need to open the liposome extrusion device and expose the contents of the liposome extrusion device to the surrounding environment.

As can be appreciated from the disclosure provided above, embodiments of the present disclosure have a wide variety of applications. Accordingly, the examples presented herein are offered for illustration purposes and are not intended to be construed as a limitation on the embodiments of the present disclosure in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

The subject methods, devices and systems find use in the preparation of a population of liposomes for therapeutic applications, such as liposomes that contain a substance, e.g., a drug, a protein, a fluorescent compound, etc., which can be used to deliver the substance to a target area in a subject. For example, the subject methods, devices and systems fid use in the preparation of a population of liposomes for drug delivery, cell therapy and in vivo applications, as well as analytical applications, such as for immune analysis.

EXAMPLES

Example 1

Experiments are performed to produce a population of liposomes according to embodiments of the present disclosure. A dry lipid mixture is prepared by lyophilization or drying under a stream of inert gas, followed by desiccation by vacuum. The dry lipids are hydrated with an aqueous solution (e.g., a buffered saline solution) for 30-60 min. For lipids with a high phase transition temperature, the aqueous solution is pre-warmed before being added to the dry lipids. If desired, the hydrated lipid suspension can be subjected to one or more freeze/thaw cycles, e.g., 3 to 5 freeze/thaw cycles, to increase the efficiency of entrapment of water-soluble compounds. For lipids with a high phase transition temperature, the liposome extrusion device is pre-warmed in a thermostatic device, if necessary. After the dry lipids are hydrated with an aqueous solution, a sample of the aqueous suspension is loaded into a liquid container of the liposome extrusion device. The liposome extrusion device is placed in the rotor of the centrifuge with the sample-loaded liquid container on top. The sample is centrifuged. The centrifugation time and speed (rpm) is varied depending on the type of membrane being used. The centrifugation is repeated if necessary, inverting the liposome extrusion device between each centrifugation of the sample by removing the liposome extrusion device from the rotor of the centrifuge, turning it over, and placing the liposome extrusion device back in the rotor. The sample-loaded liquid container is on top again, and the sample is centrifuged. The centrifugation is repeated with inversion of the liposome extrusion device as many times as necessary to produce a population of liposomes of a desired defined size.

Embodiments

The disclosure set forth herein is also defined by the following clauses:
1. A method for producing a uniform population of liposomes, the method comprising:
    introducing a suspension of liposomes into a liposome extrusion device comprising:
        a first liquid container;
        a second liquid container in fluid communication with the first liquid container;
        a porous membrane; and
        a component configured to position the membrane between the first liquid container and the second liquid container; and
    applying a centrifugal force to the suspension of liposomes in a manner sufficient to pass the liposomes through the membrane to produce a uniform population of liposomes.

2. The method according to Clause 1, wherein the introducing comprises introducing the suspension of liposomes into the first liquid container or the second liquid container.
3. The method according to Clause 2, further comprising connecting the liquid container containing the suspension of liposomes to the component.
4. The method according to Clause 3, further comprising connecting the other liquid container to the component.
5. The method according to any of Clauses 1 to 4, wherein the applying the centrifugal force is repeated one or more times.
6. The method according to Clause 5, further comprising inverting the liposome extrusion device between each repetition of the applying.
7. The method according to any of Clauses 1 to 6, wherein the applying the centrifugal force comprises spinning the liposome extrusion device in a centrifuge.
8. The method according to any of Clauses 1 to 7, wherein the applying comprises applying the centrifugal force such that the suspension of liposomes is extruded from the first liquid container into the second liquid container through the membrane, or wherein the applying comprises applying the centrifugal force such that the suspension of liposomes is extruded from the second liquid container into the first liquid container through the membrane.
9. The method according to any of Clauses 1 to 8, wherein the applying the centrifugal force is performed at atmospheric pressure.
10. The method according to any of Clauses 1 to 9, wherein the first liquid container comprises a centrifuge tube.
11. The method according to any of Clauses 1 to 10, wherein the second liquid container comprises a centrifuge tube.
12. The method according to any of Clauses 1 to 11, wherein the component comprises a first connector for connecting the component to the first liquid container.
13. The method according to Clause 12, wherein the first connector comprises screw threads and an open end of the first liquid container comprises corresponding screw threads.
14. The method according to any of Clauses 1 to 13, wherein the component comprises a second connector for connecting the component to the second liquid container.
15. The method according to Clause 14, wherein the second connector comprises screw threads and an open end of the second liquid container comprises corresponding screw threads.
16. The method according to any of Clauses 1 to 15, wherein the membrane is positioned between a first end of the component and a second end of the component.
17. The method according to any of Clauses 1 to 16, wherein the component comprises a first subcomponent and a second subcomponent removably attached to the first subcomponent.
18. The method according to Clause 17, wherein the membrane is positioned at an interface between the first subcomponent and the second subcomponent.
19. The method according to any of Clauses 1 to 18, wherein the component has an inner diameter the same as an inner diameter of the first liquid container or the second liquid container.
20. The method according to any of Clauses 1 to 19, wherein the membrane has a pore size of 1000 nm or less.
21. The method according to any of Clauses 1 to 20, wherein the membrane has a pore size of 500 nm or less.
22. The method according to any of Clauses 1 to 21, wherein the membrane has a pore size of 250 nm or less.
23. The method according to any of Clauses 1 to 22, wherein the membrane comprises one or more layers of a membrane material.
24. The method according to Clause 23, wherein the membrane material comprises a polymer.
25. The method according to Clause 24, wherein the polymer comprises polycarbonate.
26. The method according to any of Clauses 23 to 25, wherein the membrane comprises two or more layers of a membrane material.
27. The method according to Clause 26, wherein the pore size of each of the two or more layers of the membrane material is the same.
28. The method according to Clause 26, wherein the pore size of at least two of the two or more layers of the membrane material are different.
29. The method according to any of Clauses 1 to 28, further comprising preparing the suspension of liposomes.
30. The method according to any of Clauses 1 to 29, wherein the suspension of liposomes comprises a population of liposomes having heterogeneous sizes.
31. The method according to any of Clauses 1 to 30, wherein the liposomes comprise a fluorescent label.
32. The method according to any of Clauses 1 to 31, wherein the uniform population of liposomes has an average diameter of 1000 nm or less.
33. The method according to any of Clauses 1 to 32, wherein the uniform population of liposomes has an average diameter of 500 nm or less.
34. The method according to any of Clauses 1 to 33, wherein the uniform population of liposomes has an average diameter of 250 nm or less.
35. A liposome extrusion device comprising:
   a porous membrane; and
   a component configured to position the membrane between a first liquid container and a second liquid container, wherein, when the component is attached to the first liquid container and the second liquid container, an interior of the component is sealed from the surrounding atmosphere.
36. The device according to Clause 35, further comprising the first liquid container.
37. The device according to Clause 35 or 36, further comprising the second liquid container.
38. The device according to any of Clauses 35 to 37, wherein the first liquid container comprises a centrifuge tube.
39. The device according to any of Clauses 35 to 38, wherein the second liquid container comprises a centrifuge tube.
40. The device according to any of Clauses 35 to 39, wherein the component comprises a first connector for connecting the component to the first liquid container.
41. The device according to Clause 40, wherein the first connector comprises screw threads and an open end of the first liquid container comprises corresponding screw threads.

42. The device according to any of Clauses 35 to 41, wherein the component comprises a second connector for connecting the component to the second liquid container.
43. The device according to Clause 42, wherein the second connector comprises screw threads and an open end of the second liquid container comprises corresponding screw threads.
44. The device according to any of Clauses 35 to 43, wherein the membrane is positioned between a first end of the component and a second end of the component.
45. The device according to any of Clauses 35 to 44, wherein the component comprises a first subcomponent and a second subcomponent removably attached to the first subcomponent.
46. The device according to Clause 45, wherein the membrane is positioned at an interface between the first subcomponent and the second subcomponent.
47. The device according to any of Clauses 35 to 46, wherein the component has an inner diameter the same as an inner diameter of the first liquid container or the second liquid container.
48. The device according to any of Clauses 35 to 47, wherein the membrane has a pore size of 1000 nm or less.
49. The device according to any of Clauses 35 to 48, wherein the membrane has a pore size of 500 nm or less.
50. The device according to any of Clauses 35 to 49, wherein the membrane has a pore size of 250 nm or less.
51. The device according to any of Clauses 35 to 50, wherein the membrane comprises one or more layers of a membrane material.
52. The device according to Clause 51, wherein the membrane material comprises a polymer.
53. The device according to Clause 52, wherein the polymer comprises polycarbonate.
54. The device according to Clause 35 to 53, wherein the membrane comprises two or more layers of a membrane material.
55. The device according to Clause 54, wherein the pore size of each of the two or more layers of the membrane material is the same.
56. The device according to Clause 54, wherein the pore size of at least two of the two or more layers of the membrane material are different.
57. A system for producing a uniform population of liposomes, the system comprising:
a first liquid container;
a second liquid container; and
a liposome extrusion device comprising:
a porous membrane; and
a component configured to position the membrane between the first liquid container and the second liquid container, wherein, when the component is attached to the first liquid container and the second liquid container, an interior of the component is sealed from the surrounding atmosphere.
58. The system according to Clause 57, further comprising an adapter configured to contain the liposome extrusion device.
59. The system according to Clause 58, wherein the adapter comprises a cylinder with an outer surface concentric to an interior surface of a centrifuge tube holder of a centrifuge.
60. The system according to any of Clauses 57 to 59, wherein the liposome extrusion device contains a suspension of liposomes.
61. The system according to any of Clauses 57 to 60, further comprising a centrifuge.
62. The system according to any of Clauses 57 to 61, wherein the first liquid container comprises a centrifuge tube.
63. The system according to any of Clauses 57 to 62, wherein the second liquid container comprises a centrifuge tube.
64. The system according to any of Clauses 57 to 63, wherein the first liquid container comprises a centrifuge tube.
65. The system according to any of Clauses 57 to 64, wherein the second liquid container comprises a centrifuge tube.
66. The system according to any of Clauses 57 to 65, wherein the component comprises a first connector for connecting the component to the first liquid container.
67. The system according to Clause 66, wherein the first connector comprises screw threads and an open end of the first liquid container comprises corresponding screw threads.
68. The system according to any of Clauses 57 to 67, wherein the component comprises a second connector for connecting the component to the second liquid container.
69. The system according to Clause 68, wherein the second connector comprises screw threads and an open end of the second liquid container comprises corresponding screw threads.
70. The system according to any of Clauses 57 to 69, wherein the membrane is positioned between a first end of the component and a second end of the component.
71. The system according to any of Clauses 57 to 70, wherein the component comprises a first subcomponent and a second subcomponent removably attached to the first subcomponent.
72. The system according to Clause 71, wherein the membrane is positioned at an interface between the first subcomponent and the second subcomponent.
73. The system according to any of Clauses 57 to 72, wherein the component has an inner diameter the same as an inner diameter of the first liquid container or the second liquid container.
74. The system according to any of Clauses 57 to 73, wherein the membrane has a pore size of 1000 nm or less.
75. The system according to any of Clauses 57 to 74, wherein the membrane has a pore size of 500 nm or less.
76. The system according to any of Clauses 57 to 75, wherein the membrane has a pore size of 250 nm or less.
77. The system according to any of Clauses 57 to 76, wherein the membrane comprises one or more layers of a membrane material.
78. The system according to Clause 77, wherein the membrane material comprises a polymer.
79. The system according to Clause 78, wherein the polymer comprises polycarbonate.
80. The system according to Clause 57 to 79, wherein the membrane comprises two or more layers of a membrane material.

81. The system according to Clause 80, wherein the pore size of each of the two or more layers of the membrane material is the same.
82. The system according to Clause 80, wherein the pore size of at least two of the two or more layers of the membrane material are different.
83. A kit comprising:
a liposome extrusion device comprising:
a porous membrane; and
a component configured to position the membrane between a first liquid container and a second liquid container, wherein, when the component is attached to the first liquid container and the second liquid container, an interior of the component is sealed from the surrounding atmosphere; and a packaging configured to hold the device.
84. The kit according to Clause 83, further comprising an adapter configured to contain the liposome extrusion device.
85. The system according to Clause 84, wherein the adapter comprises a cylinder with an outer surface concentric to an interior surface of a centrifuge tube holder of a centrifuge.
86. The kit according to any of Clauses 83 to 85, further comprising a set of standard fluorescently labelled beads.
87. The kit according to any of Clauses 83 to 86, further comprising the first liquid container.
88. The kit according to any of Clauses 83 to 87, further comprising the second liquid container.
89. The kit according to any of Clauses 83 to 88, wherein the first liquid container comprises a centrifuge tube.
90. The kit according to any of Clauses 83 to 89, wherein the second liquid container comprises a centrifuge tube.
91. The kit according to any of Clauses 83 to 90, wherein the component comprises a first connector for connecting the component to the first liquid container.
92. The kit according to Clause 91, wherein the first connector comprises screw threads and an open end of the first liquid container comprises corresponding screw threads.
93. The kit according to any of Clauses 83 to 92, wherein the component comprises a second connector for connecting the component to the second liquid container.
94. The kit according to Clause 93, wherein the second connector comprises screw threads and an open end of the second liquid container comprises corresponding screw threads.
95. The kit according to any of Clauses 83 to 94, wherein the membrane is positioned between a first end of the component and a second end of the component.
96. The kit according to any of Clauses 83 to 95, wherein the component comprises a first subcomponent and a second subcomponent removably attached to the first subcomponent.
97. The kit according to Clause 96, wherein the membrane is positioned at an interface between the first subcomponent and the second subcomponent.
98. The kit according to any of Clauses 83 to 97, wherein the component has an inner diameter the same as an inner diameter of the first liquid container or the second liquid container.
99. The kit according to any of Clauses 83 to 98, wherein the membrane has a pore size of 1000 nm or less.
100. The kit according to any of Clauses 83 to 99, wherein the membrane has a pore size of 500 nm or less.
101. The kit according to any of Clauses 83 to 100, wherein the membrane has a pore size of 250 nm or less.
102. The kit according to any of Clauses 83 to 101, wherein the membrane comprises one or more layers of a membrane material.
103. The kit according to Clause 102, wherein the membrane material comprises a polymer.
104. The kit according to Clause 103, wherein the polymer comprises polycarbonate.
105. The kit according to Clause 83 to 104, wherein the membrane comprises two or more layers of a membrane material.
106. The kit according to Clause 105, wherein the pore size of each of the two or more layers of the membrane material is the same.
107. The kit according to Clause 105, wherein the pore size of at least two of the two or more layers of the membrane material are different.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of embodiments of the present disclosure. It will be appreciated that those skilled in the art will be able to devise various arrangements which, although not explicitly described or shown herein, embody the principles of embodiments of the present disclosure and are included within its spirit and scope. Furthermore, all examples and conditional language recited herein are principally intended to aid the reader in understanding the principles of embodiments of the present disclosure being without limitation to such specifically recited examples and conditions. Moreover, all statements herein reciting principles, aspects, and embodiments of embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the embodiments of the present disclosure, therefore, is not intended to be limited to the exemplary embodiments shown and described herein. Rather, the scope and spirit of embodiments of the present disclosure are embodied by the appended claims.

What is claimed is:
1. A liposome extrusion device comprising:
a first liquid container comprising a single opening;
a second liquid container comprising a single opening;
a porous membrane; and
a component configured to position the membrane between the first liquid container and the second liquid container, wherein, when the component is attached to the single opening of the first liquid container and the single opening of the second liquid container, an interior of the component is sealed from the surrounding atmosphere.
2. The device according to claim 1, wherein the first liquid container comprises a centrifuge tube.
3. The device according to claim 1, wherein the second liquid container comprises a centrifuge tube.

4. The device according to claim 1, wherein the membrane is positioned between a first end of the component and a second end of the component.

5. The device according to claim 1, wherein the component comprises a first subcomponent and a second subcomponent removably attached to the first subcomponent.

6. The device according to claim 5, wherein the membrane is positioned at an interface between the first subcomponent and the second subcomponent.

7. The device according to claim 1, wherein the membrane has a pore size of 1000 nm or less.

8. The device according to claim 1, wherein the membrane comprises two or more layers of a membrane material.

9. The device of claim 1, wherein the porous membrane comprises pores that pass through the membrane without intersecting other pores in the membrane.

10. The device of claim 1, wherein the porous membrane comprises a membrane material that does not react with liquid or liposomes contacted to the membrane.

11. A kit comprising:
a liposome extrusion device comprising:
a first liquid container comprising a single opening;
a second liquid container comprising a single opening;
a porous membrane; and
a component configured to position the membrane between the first liquid container and the second liquid container, wherein, when the component is attached to the single opening of the first liquid container and the single opening of the second liquid container, an interior of the component is sealed from the surrounding atmosphere; and
a packaging configured to hold the device.

12. The kit according to claim 11, further comprising an adapter configured to contain the liposome extrusion device.

13. The system according to claim 12, wherein the adapter comprises a cylinder with an outer surface concentric to an interior surface of a centrifuge tube holder of a centrifuge.

* * * * *